(12) United States Patent
Parsons et al.

(10) Patent No.: US 9,829,378 B1
(45) Date of Patent: Nov. 28, 2017

(54) DETERMINING A SIZE OF CELL OF A TRANSMISSION SPECTROSCOPY DEVICE

(71) Applicant: Bentley Instruments, Inc., Chaska, MN (US)

(72) Inventors: Craig Parsons, Shorewood, MN (US); Henrik Lyder, Chaska, MN (US)

(73) Assignee: Bentley Instruments, Inc., Chaska, MN (US)

( * ) Notice: Subject to any disclaimer, the term of this patent is extended or adjusted under 35 U.S.C. 154(b) by 0 days.

(21) Appl. No.: 15/292,593

(22) Filed: Oct. 13, 2016

(51) Int. Cl.
*G01N 21/00* (2006.01)
*G01J 3/02* (2006.01)
*G01J 3/42* (2006.01)
*G01B 11/02* (2006.01)

(52) U.S. Cl.
CPC .............. *G01J 3/027* (2013.01); *G01B 11/02* (2013.01); *G01J 3/0267* (2013.01); *G01J 3/42* (2013.01)

(58) Field of Classification Search
CPC .. G01N 21/253; G01N 21/0303; G01N 21/05; G01N 21/03; G01N 30/74
USPC ........................................................ 356/440
See application file for complete search history.

(56) References Cited

U.S. PATENT DOCUMENTS

| | | | |
|---|---|---|---|
| 4,998,017 A | 3/1991 | Ryan et al. | |
| 5,267,019 A | 11/1993 | Whittake et al. | |
| 6,115,673 A | 9/2000 | Malin et al. | |
| 6,654,125 B2 | 11/2003 | Maynard | |
| 7,009,180 B2 | 3/2006 | Sterling et al. | |
| 7,057,164 B2 | 6/2006 | Springsteen et al. | |
| 7,079,252 B1 | 7/2006 | Debreczeny et al. | |
| 7,096,124 B2 | 8/2006 | Sterling et al. | |
| 7,251,037 B2 | 7/2007 | Jones | |
| 7,704,301 B2 | 4/2010 | Zhou et al. | |

(Continued)

FOREIGN PATENT DOCUMENTS

WO WO-2016132222 A2 8/2016

OTHER PUBLICATIONS

"Cell Calibration", International Crystal Laboratories, [Online]. Retrieved from the Internet: <URL: http://www.internationalcrystal.net/ti_sec4.htm, (accessed Oct. 6, 2016), 3 pgs.

(Continued)

*Primary Examiner* — Tarifur Chowdhury
*Assistant Examiner* — Md M Rahman
(74) *Attorney, Agent, or Firm* — Schwegman Lundberg & Woessner, P.A.

(57) ABSTRACT

A transmission spectroscopy device can direct light into a sample, and determine properties of the sample based on how much light emerges from the sample. The device can use a cell to contain the sample, so that the size of the cell defines the optical path length traversed by light in the sample. To ensure accuracy in the measurements, it is beneficial to calibrate the device by measuring the size of the cell periodically or as needed. To measure the size of the cell, the device can perform a transmission spectroscopy measurement of a known substance, such as pure water, to produce a measured absorbance spectrum of the known substance. The device can subtract a known absorbance spectrum of the known substance from the measured absorbance spectrum to form an oscillatory fringe pattern. The device can determine the size of the cell from a period of the fringe pattern.

8 Claims, 7 Drawing Sheets

(56) References Cited

U.S. PATENT DOCUMENTS

| | | |
|---|---|---|
| 8,018,981 B2 | 9/2011 | Eckles et al. |
| 8,223,338 B2 | 7/2012 | Robertson, Jr. et al. |
| 8,363,224 B2 | 1/2013 | Maity et al. |
| 9,007,591 B2 | 4/2015 | Arimoto et al. |
| 9,097,583 B2 | 8/2015 | Gupta et al. |
| 9,109,951 B2 | 8/2015 | Scott et al. |
| 9,170,191 B2 | 10/2015 | Coffin et al. |
| 2005/0124870 A1* | 6/2005 | Lipson ............... G01J 3/02 600/316 |
| 2007/0279628 A1* | 12/2007 | Lipson ............... G01J 3/02 356/317 |
| 2012/0261578 A1 | 10/2012 | Scott et al. |
| 2013/0276509 A1 | 10/2013 | Rathke et al. |
| 2016/0123870 A1 | 5/2016 | Hansen |

OTHER PUBLICATIONS

"Transmission Sampling Techniques—Theory and Applications", Pike Technologies, [Online]. Retrieved from the Internet: <URL: http://www.piketech.com/files/pdfs/TransmissionAN611.pdf, (2011), 3 pgs.

Nwaboh, Javis Anyangwe, et al., "Optical Path Length Calibration: A Standard Approach for Use in Absorption Cell-Based IR-Spectrometric Gas Analysis", International Journal of Spectroscopy vol. 2014 (2014), Article ID 132607, [Online]. Retrieved from the Internet: <URL: https://www.hindawi.com/journals/ijs/2014/132607/, (2014), 7 pgs.

\* cited by examiner

DETERMINING A SIZE OF CELL OF A TRANSMISSION SPECTROSCOPY DEVICE

FIELD OF THE DISCLOSURE

The present disclosure relates to calibration of a transmission spectroscopy device.

BACKGROUND OF THE DISCLOSURE

Transmission spectroscopy is widely used for quantitatively measuring components of gaseous, liquid and solid substances. A transmission spectroscopy device can direct light into a sample, and determine properties of the sample based on how much light emerges from the sample, as a function of wavelength.

In some examples, a transmission spectroscopy device can base its calculations on the Beer-Lambert law, which relates the attenuation of light to properties of the material through which the light propagates. One way to express the Beer-Lambert law mathematically is $A = e \times b \times c$. Quantity A is the absorbance of the sample, which also equals log (1/transmittance of the sample). Quantity e is the molar absorptivity of a compound of interest in the sample. Quantity b is the optical path length traversed by light in the sample. Quantity c is the concentration of the compound of interest in the sample. In order to produce an accurate value for the compound concentration, c, one should have an accurate value for the optical path length traversed by light in the sample, b. The Beer-Lambert law is but one example of how a transmission spectroscopy device can perform its calculations. Other calculation techniques can also be used. For each of these calculation techniques, it is beneficial to know or measure the optical path length traversed by light in the sample as accurately as possible.

SUMMARY

In a first example, a method for determining a size of a cell of a transmission spectroscopy device can include performing a transmission spectroscopy measurement of a known substance in a cell to produce a measured absorbance spectrum of the known substance. The measured absorbance spectrum of the known substance can be formed from a ratio of a first emittance scan of the cell to a second emittance scan of the cell. The first emittance scan can be taken when the cell is filled with the known substance. The second emittance scan can be taken when the cell is empty. The method can further include subtracting a known absorbance spectrum of the known substance from the measured absorbance spectrum of the known substance to form a fringe pattern. The fringe pattern can be oscillatory in amplitude with respect to inverse wavelength. The method can further include determining a size of the cell from a period of the fringe pattern.

In a second example, a transmission spectroscopy device can include a cell having opposing first and second transparent walls. The cell can be fillable with a sample to be measured. The cell can be drainable to remove the sample and replace the sample with air. Plumbing can deliver the sample to the cell and drain the sample from the cell. A light source can illuminate the sample through the first transparent wall. A detector can detect light transmitted through the sample through the second transparent wall. A controller can operably control the light source, operably receive at least one signal from the detector, and operably control the plumbing. The controller can fill the cell with the sample, produce a measured absorbance spectrum of the sample, and drain the sample from the cell. The controller can further calibrate the transmission spectroscopy device by: producing a measured absorbance spectrum of a pure water sample, the measured absorbance spectrum of the pure water sample formed from a ratio of a first emittance scan of the cell to a second emittance scan of the cell, the first emittance scan taken when the cell is filled with the pure water sample, the second emittance scan taken when the cell is empty; subtracting a known absorbance spectrum of water from the measured absorbance spectrum of the pure water sample to form a fringe pattern, the fringe pattern being oscillatory in amplitude with respect to inverse wavelength; and calculating the separation between the first and second transparent walls to equal $1/(2 \times p)$, where quantity p is a period of the fringe pattern.

In a third example, a method for determining a size of cell of a transmission spectroscopy device can include performing a transmission spectroscopy measurement of a pure water sample in a cell to produce a measured absorbance spectrum of the pure water sample. The measured absorbance spectrum of the pure water sample can be formed from a ratio of a first emittance scan of the cell to a second emittance scan of the cell. The first emittance scan can be taken when the cell is filled with the pure water sample. The second emittance scan can be taken when the cell is empty. The method can further include subtracting a known absorbance spectrum of water from the measured absorbance spectrum of the pure water sample to form a fringe pattern. The fringe pattern can be oscillatory in amplitude with respect to inverse wavelength. The method can further include calculating a separation between opposing first and second transparent walls of the cell to equal $1/(2 \times p)$, where quantity p is a period of the fringe pattern.

BRIEF DESCRIPTION OF THE DRAWINGS

Corresponding reference characters indicate corresponding parts throughout the several views. Elements in the drawings are not necessarily drawn to scale. The configurations shown in the drawings are merely examples, and should not be construed as necessarily limiting the scope of the claims.

DETAILED DESCRIPTION

In transmission spectroscopy, it is beneficial to know or measure the optical path length traversed by light in the sample as accurately as possible. For gaseous or liquid samples, a transmission spectroscopy device can use a cell or cuvette to contain the sample. The cell can include two opposing, transparent walls. During a measurement, light enters the cell through one of the transparent walls, passes through the sample, and exits the cell through the other of the transparent walls. The size of the cell defines the optical path length traversed by light in the sample. In some examples, the size of the cell can refer to a cell width, a cell length, or another suitable cell dimension. To ensure accuracy in the measurements, it is beneficial to calibrate the transmission spectroscopy device by measuring the size of the cell periodically or as needed.

To measure the size of the cell, the device can perform a transmission spectroscopy measurement of a known substance, such as pure water, to produce a measured absorbance spectrum of the known substance. The device can subtract a known absorbance spectrum of the known substance from the measured absorbance spectrum to form an oscillatory fringe pattern. The fringes can be Fabry-Perot fringes, caused by interference from reflections from two parallel surfaces. The fringes can be present in the measured absorption spectrum, but masked by larger absorbance effects. Subtracting the known absorbance spectrum from the measured absorbance spectrum can remove or reduce the absorbance effects, and can emphasize the fringe pattern in the measured absorption spectrum. The device can determine the size of the cell from a period of the fringe pattern. This is but a summary of a technique to measure the size of the cell; the technique is discussed below in more detail, following a description of a transmission spectroscopy device.

Figure 1:
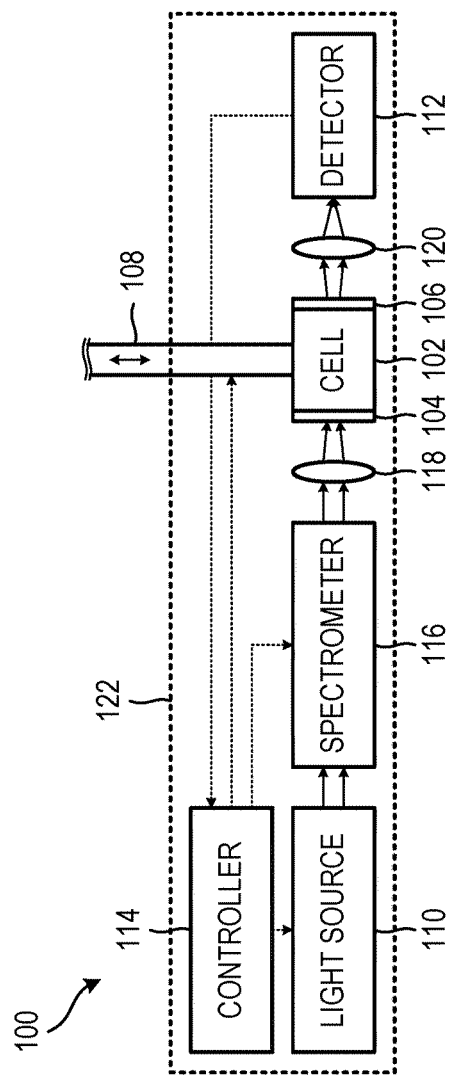
FIG. 1 shows a schematic drawing of an example of a transmission spectroscopy device, in accordance with some embodiments.

FIG. 1 shows a schematic drawing of an example of a transmission spectroscopy device 100, in accordance with some embodiments. The transmission spectroscopy device 100 is but one example of a device that can use the technique described herein to measure the size of the cell; other devices can also be used.

A cell 102 can have a first transparent wall 104 and a second transparent wall 106 opposing the first transparent wall 104. The cell 102 can be fillable with a sample to be measured. The sample is not part of the part of the transmission spectroscopy device 100. The cell can be drainable to remove the sample and replace the sample with air. In some examples, the first transparent wall 104 and the second transparent wall 106 can be formed from glass, calcium fluoride, or other suitable materials selected to be insoluble with respect to the sample. In some examples, the first transparent wall 104 and the second transparent wall 106 can have a nominal separation between 10 µm and 50 µm.

In some examples, the separation between the first transparent wall 104 and the second transparent wall 106 can vary slightly over time. For example, the separation can increase slightly if the first transparent wall 104 and the second transparent wall 106 are eroded by continual use. Likewise, the separation can decrease slightly if samples cause a buildup of material on the first transparent wall 104 and the second transparent wall 106. The technique described herein to measure the size of the cell 102 can track the cell size variation over time, and can allow the transmission spectroscopy device 100 to properly account for cell size and perform accurate measurements. The cell size measurement technique can be used as a calibration routine, which can be executed periodically, such as once a day, or once for every thousand measurements.

Plumbing 108 can deliver the sample to the cell 102 and can drain the sample from the cell 102. The plumbing 108 can include one or more pipes, hoses, valves, pumps, and other elements can direct fluids or gases as needed. The plumbing 108 can include one or more connections to the cell 102. In some examples, the plumbing 108 can direct the sample into or out of the transmission spectroscopy device 100, and can connect to one or more elements outside the transmission spectroscopy device 100. In some examples, the plumbing 108 can deliver air to the cell 102. In some examples, the plumbing 108 can pump air to the cell 102, to drain the cell of a sample.

A light source 110 can illuminate the sample through the first transparent wall 104. In some examples, the light source 110 can be a broadband light source, such as a blackbody source, an incandescent source, one or more light emitting diodes, or other suitable light sources. In some examples, the light source 110 produces a collimated output beam. In some examples, the light source 110 includes one or more collimating lenses, which can collimate light from a diverging source, such as a light emitting diode, to produce a collimated output beam. In some examples, the light source 110 can emit light in the mid-infrared portion of the spectrum. In some examples, the light source 110 can emit light with wavelengths between 1.25 µm and 12.5 µm, or, equivalently, inverse wavelengths between 800 $cm^{-1}$ (corresponding to 12.5 µm) and 8000 $cm^{-1}$ (corresponding to 1.25 µm). Other wavelength ranges can also be used, including the visible portion of the spectrum, the near-infrared portion of the spectrum, or the far infrared portion of the spectrum.

A detector 112 can detect light transmitted through the sample through the second transparent wall 106. In some examples, the detector 112 is sensitive in the wavelength range emitted by the light source 110.

A controller 114 can operably control the light source 110, operably receive at least one signal from the detector 112, and operably control the plumbing 108. During execution of the cell size measurement technique, the controller 114 can fill the cell 102 with the sample, produce a measured absorbance spectrum of the sample, and drain the sample from the cell 102. In some examples, the controller 114 can include a processor and memory, including instructions that, when executed on the at least processor, cause the processor to execute the technique to measure the size of the cell.

The transmission spectroscopy device 100 can further include a spectrometer 116 that can receive light emitted from the light source 110, and can analyze the received light as a function of wavelength. In some examples, the spectrometer 116 can include a diffraction grating, a prism, or another optical element capable of spatially or angularly dispersing light as a function of wavelength. In some examples, in a configuration referred to as dispersive spectroscopy, the spectrometer 116 has a selectable output wavelength (or narrow band of wavelengths), which can be controlled by the controller 114, and can vary over time. The controller 114 can correlate the wavelength output of the spectrometer, over time, with the signal received at the detector 112, to measure a sample in the cell 102 as a function of wavelength. In other examples, the spectrometer can analyze the wavelength dependence of the transmitted light signal by generating an interferogram produced by the varying the optical path length of two interfering light beams. The Fourier transform of this interferogram results in a spectrum of intensity vs. wavelength (or energy, often in units of 1/wavelength). This technique is referred to as Fourier Transform Spectroscopy, and has several advantages over dispersive spectroscopy in terms of optical throughput and wavelength multiplexing. Positioning the spectrometer 116 between the light source 110 and the cell 102 is but one configuration. Other configurations can also be used, such as positioning the spectrometer 116 between the cell 102 and the detector 112, using a multi-element detector to simultaneously capture light at different wavelengths for the dispersive technique, and others. The spectrometer 116 can receive and output collimated light.

The transmission spectroscopy device 100 can further include a lens 118 that can focus light from the spectrometer 116 onto the cell 102, and a lens 120 that can focus light from the cell onto the detector 112. The lens 118 can allow the transmission spectroscopy device 100 to use a relatively small cell 102, which can advantageously take measurements of samples having a relatively small volume. The lens 120 can allow the transmission spectroscopy device 100 to use a relatively small detector 112, which can advantageously reduce noise associated with the detector 112 and can increase the speed of the detector 112.

The transmission spectroscopy device 100 can further include a housing 122, which can ensure that the cell 102 operates in an environment that is stable over time. For example, the housing 122 can control the temperature and pressure of the sample in the cell 102. The housing 122 can maintain a constant composition of the gases, such as water vapor and carbon dioxide, around the cell 102 and the optical elements. The housing 122 can be sealed from the ambient environment. The housing 122 can be temperature-regulated. The housing 122 can include a desiccant to reduce water vapor to a relatively low and stable level. Stabilizing the environmental variables of temperature, pressure and the composition of the gases in the optical path can increase a precision of the measurements. Stabilizing these parameters can stabilize the optical alignment of the spectrometer, which can increase the precision of the measurements.

Figure 2:
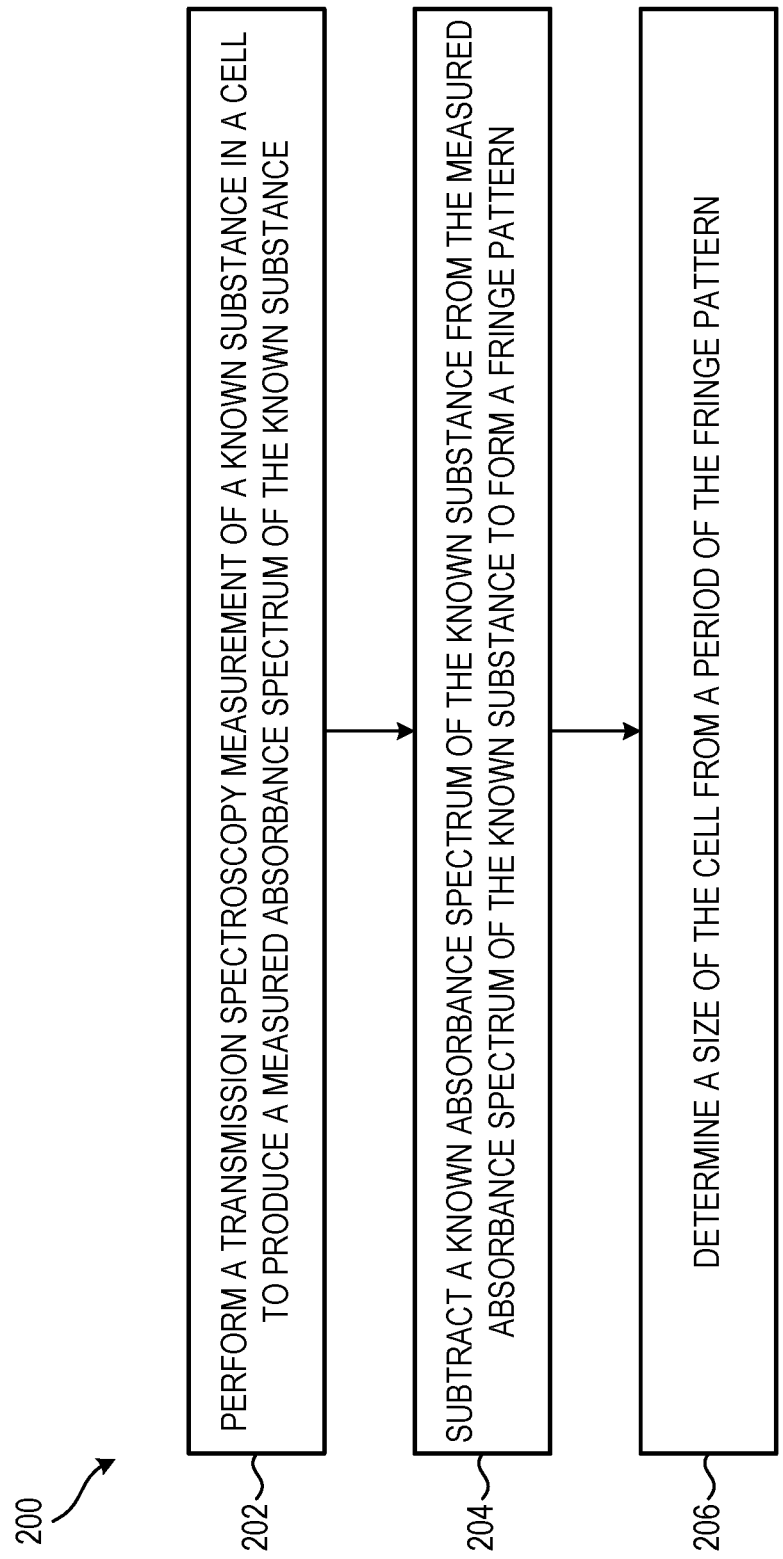
FIG. 2 shows a flowchart of an example of a method for determining a size of a cell of a transmission spectroscopy device, in accordance with some embodiments.

FIG. 2 shows a flowchart of an example of a method 200 for determining a size of a cell of a transmission spectroscopy device 100, in accordance with some embodiments. The method 200 can be executed on a transmission spectroscopy device, such as device 100 (described above with reference to FIG. 1), or on other suitable transmission spectroscopy devices. The method 200 is but one example of determining the size of the cell; other suitable methods can also be used.

At operation 202, the device 100 can perform a transmission spectroscopy measurement of a known substance in a cell 102 to produce a measured absorbance spectrum of the known substance. The measured absorbance spectrum of the known substance can be formed from a ratio of a first emittance scan of the cell 102 to a second emittance scan of the cell 102. The first emittance scan can be taken when the cell 102 is filled with the known substance. The second emittance scan can be taken when the cell 102 is empty (e.g., filled with air).

At operation 204, the device 100 can subtract a known absorbance spectrum of the known substance from the measured absorbance spectrum of the known substance to form a fringe pattern. In some examples, the known absorbance spectrum can be stored locally and can be access via a lookup table. In other examples, the known absorbance spectrum can be accessed remotely through a wired or wireless network. In some examples, the known absorbance spectrum can be obtained from an earlier transmission spectroscopy measurement of a particular sample (e.g., not necessarily a sample having a tabulated absorbance spectrum).

The fringe pattern can be caused by interference between opposing first and second transparent walls 104, 106 of the cell 102. The fringe pattern peaks when there is constructive interference between the first and second transparent walls 104, 106 of the cell 102, which occurs when the round-trip optical path between the first and second transparent walls 104, 106 equals an integral number of wavelengths. In general, the fringe pattern is smaller in amplitude than the features in the measured absorbance spectrum, so that subtracting the known absorbance spectrum of the known substance from the measured absorbance spectrum can enhance the fringe pattern. The fringe pattern can be oscillatory in amplitude with respect to inverse wavelength. In some examples, the device 100 can scale an amplitude of one of the known absorbance spectrum or the measured absorbance spectrum to match an amplitude of the other of the known absorbance spectrum or the measured absorbance spectrum.

At operation 206, the device 100 can determine a size of the cell 102 from a period of the fringe pattern. In some examples, the device 100 can calculate a separation between opposing first and second transparent walls 104, 106 of the cell 102 to equal $1/(2 \times p)$, where quantity p is a period of the fringe pattern. In some examples, the device 100 can determine inverse wavelength values at which the fringe pattern peaks, and calculate the period to equal a separation between adjacent determined inverse wavelength values. In some examples, the device 100 can fit the determined inverse wavelength values to a linear fit, determine a slope of the linear fit, and set the period equal to the determined slope.

In some examples, performing the transmission spectroscopy measurement of the known substance in the cell 102 can include the following. The device 100 can fill the cell 102 with the known substance. The device 100 can illuminate the known substance through a first transparent wall 104 of the cell 102. In some example, the illuminating light has a broad spectrum. The device 100 can measure a first light from the known substance through a second transparent wall 106 of the cell 102, opposite the first transparent wall 104. The device 100 can produce, from the first light, the first emittance scan. The device 100 can drain the known substance from the cell 102. The device 100 can fill the cell 102 with air. The device 100 can illuminate the air-filled cell 102 through the first transparent wall 104 of the cell 102. In some example, the illuminating light for the air-filled cell can have the same broad spectrum as the illuminating light used for the known substance. The device 100 can measure a second light from the air-filled cell 102 through the second transparent wall 106 of the cell 102. The device 100 can produce, from the second light, the second emittance scan. In some configurations, the device 100 can measure the sample before measuring the air-filled cell; in other configurations, the device 100 can measure the sample after measuring the air-filled cell.

In some examples, draining the known substance from the cell 102 can include, repeatedly: pumping air through the cell 102; illuminating the cell 102 through the first transparent wall 104 of the cell 102; measuring a third light through the second transparent wall 106 of the cell 102; and comparing the third light to a previous measurement of the third light, until a difference between successive measurements of the third light is below a threshold. As the cell 102 dries out, the amount of light passing through the cell reaches a constant level.

In some examples, the known substance can be pure water, although other known substances can also be used. For these examples, the broad spectrum of the illuminating light can include at least one peak or valley in the known absorbance spectrum of water. For example, in the near-infrared and mid-infrared wavelength ranges, liquid water has absorption bands around 1640 cm$^{-1}$ (corresponding to a wavelength of 6100 nm), 2130 cm$^{-1}$ (4690 nm), 3450 cm$^{-1}$ (2900 nm), and 5128 cm$^{-1}$ (1950 nm). It is convenient to use values of inverse wavelength, rather than wavelength, because the fringes in the fringe pattern are equally spaced with respect to inverse wavelength.

Figure 3:
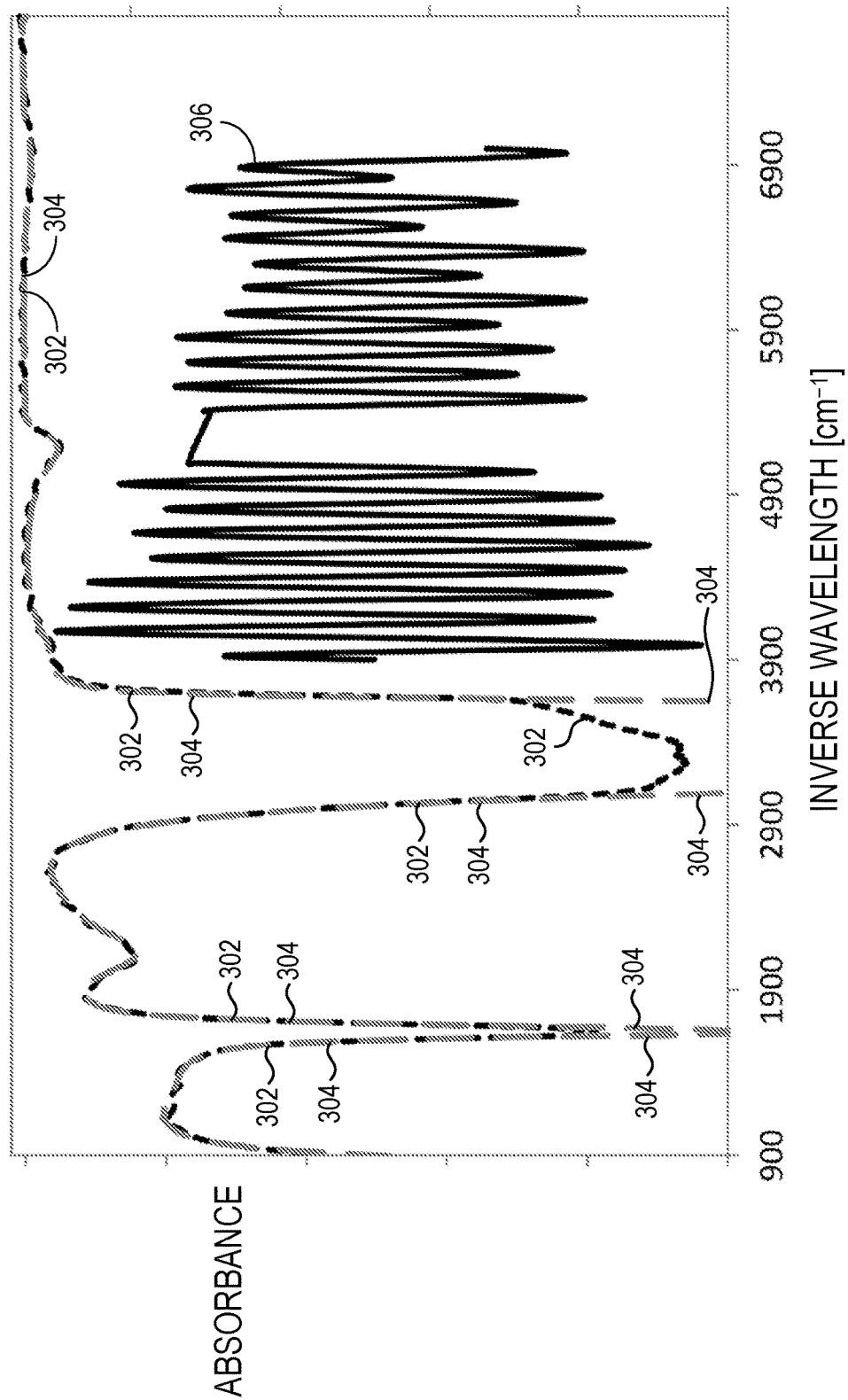
FIG. 3 shows an example of a plot of measured absorbance spectrum of water, a known absorbance spectrum of water, and a fringe pattern, in accordance with some embodiments.

FIG. 3 shows an example of a plot of a measured absorbance spectrum 302 of water, a known absorbance spectrum 304 of water, and a fringe pattern 306, in accordance with some embodiments. The measured absorbance spectrum 302 and the known absorbance spectrum 304 overlap significantly; the element numbers 302 and 304 follow the respective plots in FIG. 3. In practice, the fringe pattern 306 is present in the measured absorbance spectrum 302, but with a significantly smaller amplitude than the absorption features. Subtracting the known absorbance spectrum 304 from the measured absorbance spectrum 302 of water (optionally with scaling of one or both absorbance spectra) can enhance the fringe pattern 306. In this example, the fringe pattern extends from about 3900 cm$^{-1}$ to about 6900 cm$^{-1}$, with a discontinuity in the fringe pattern around water's absorption band at 5128 cm$^{-1}$.

The period of the fringe pattern can be determined in many suitable manners, including Fourier transforming the fringe pattern and locating a peak in the Fourier transform, finding peaks in the fringe and determining separation between the peaks, finding valleys in the fringe pattern and determining separation between the valleys, finding zero-crossings in the fringe patterns and determining separation between the zero-crossings, and others.

One suitable way to calculate the period includes: determining inverse wavelength values at which the fringe pattern peaks; fitting the determined inverse wavelength values to a linear fit; determining a slope of the linear fit; and setting the period equal to the determined slope.

Figure 4:
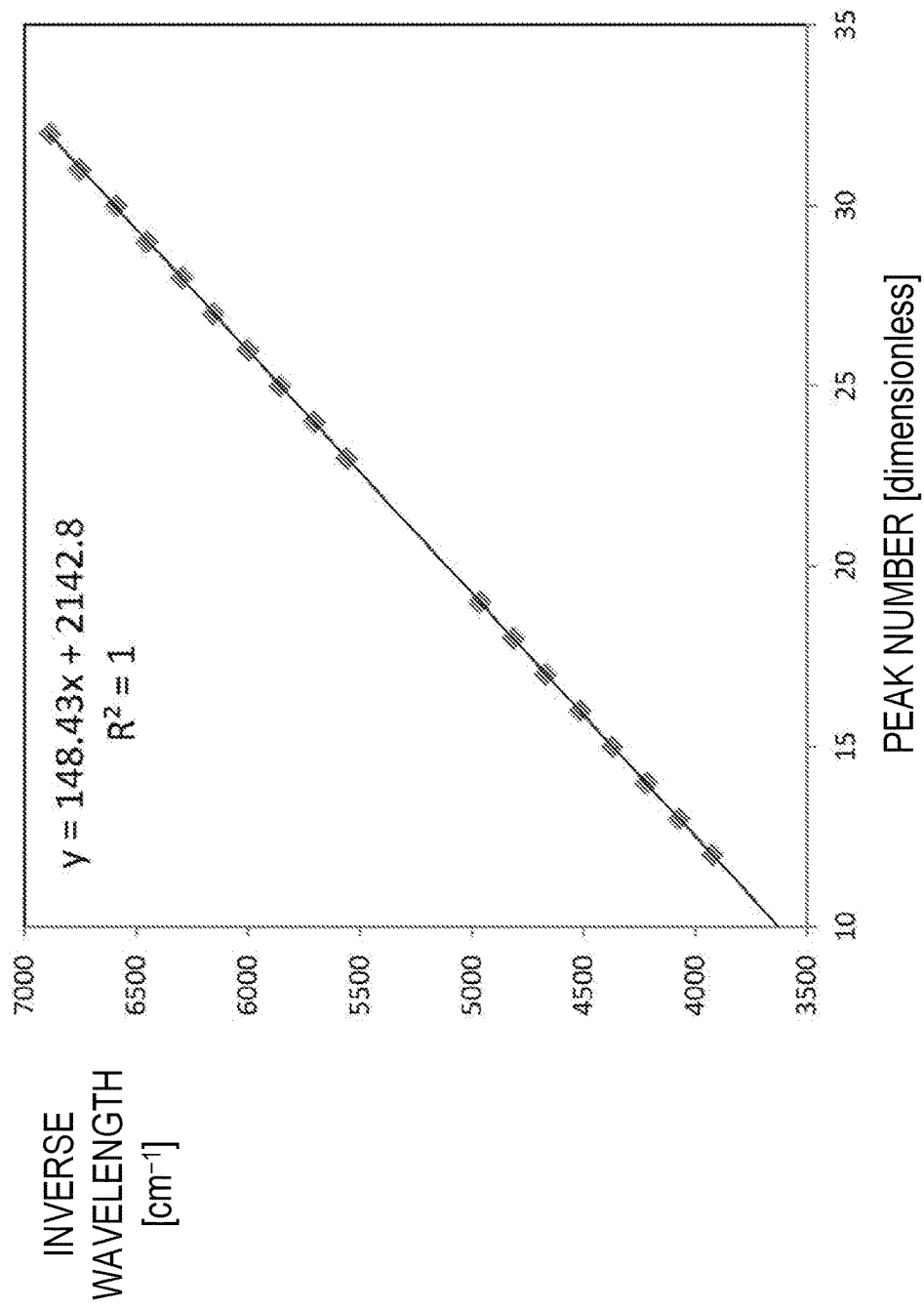
FIG. 4 shows an example of a plot of the inverse wavelength values at which the fringe pattern of FIG. 3 peaks, plotted along a linear scale by dimensionless peak number.

FIG. 4 shows an example of a plot of the inverse wavelength values at which the fringe pattern of FIG. 3 peaks, plotted along a linear scale by dimensionless peak number. The inverse wavelength values are fit to a linear fit, according to the equation: y [in cm$^{-1}$]=148.43x+2142.8. The slope of the linear fit is 148.43 cm$^{-1}$, which equals the period of the fringe pattern. In this numerical example, the separation between opposing first and second transparent walls 104, 106 of the cell 102 equals 1/(2×148.43 cm$^{-1}$), or 33.69 μm. This is but one example; other suitable numerical examples can also be used.

Figure 5:
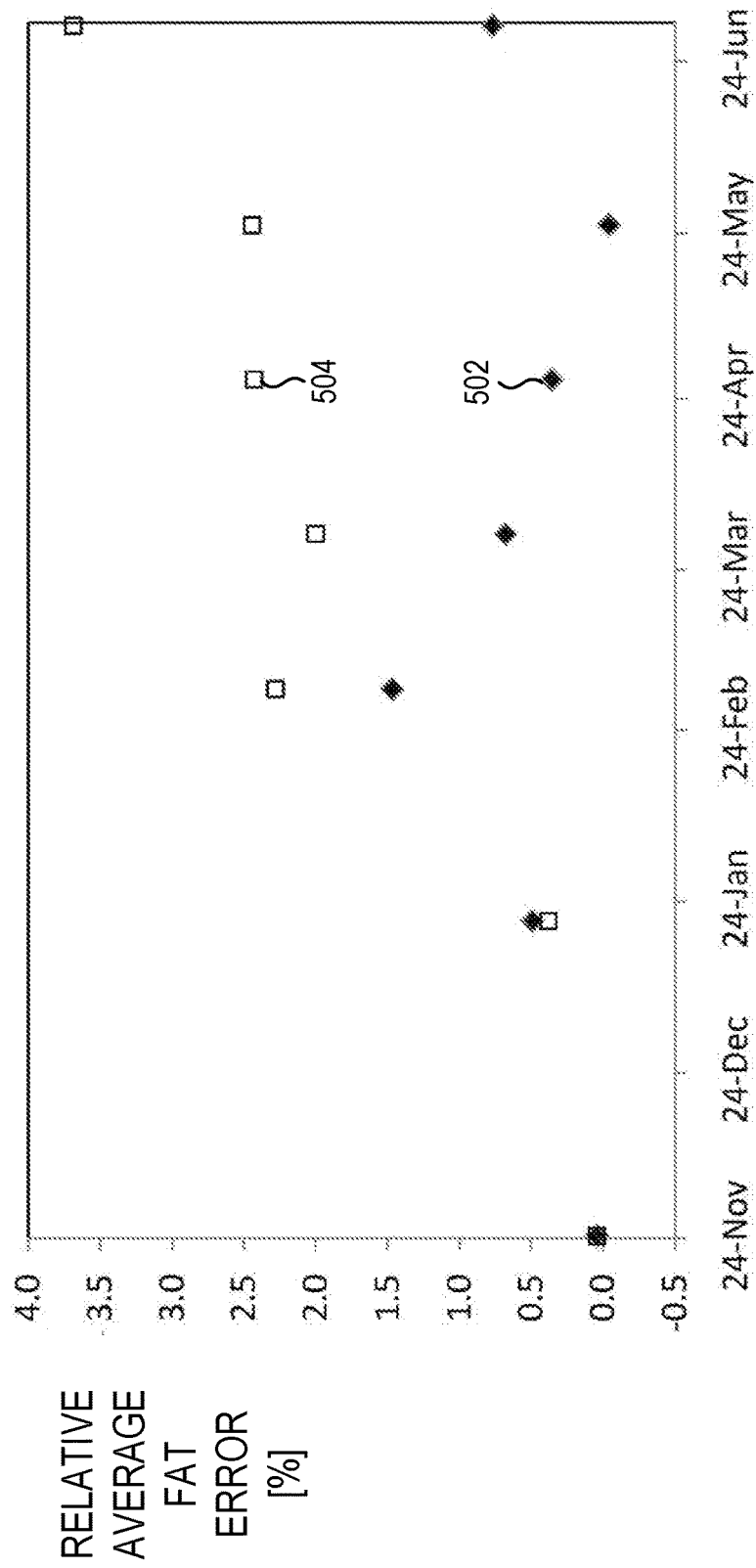
FIG. 5 shows a relative fat error, in percent, for measurements in which the cell width was periodically measured, and corresponding measurements in which the cell width was not periodically measured or updated.
Figure 6:
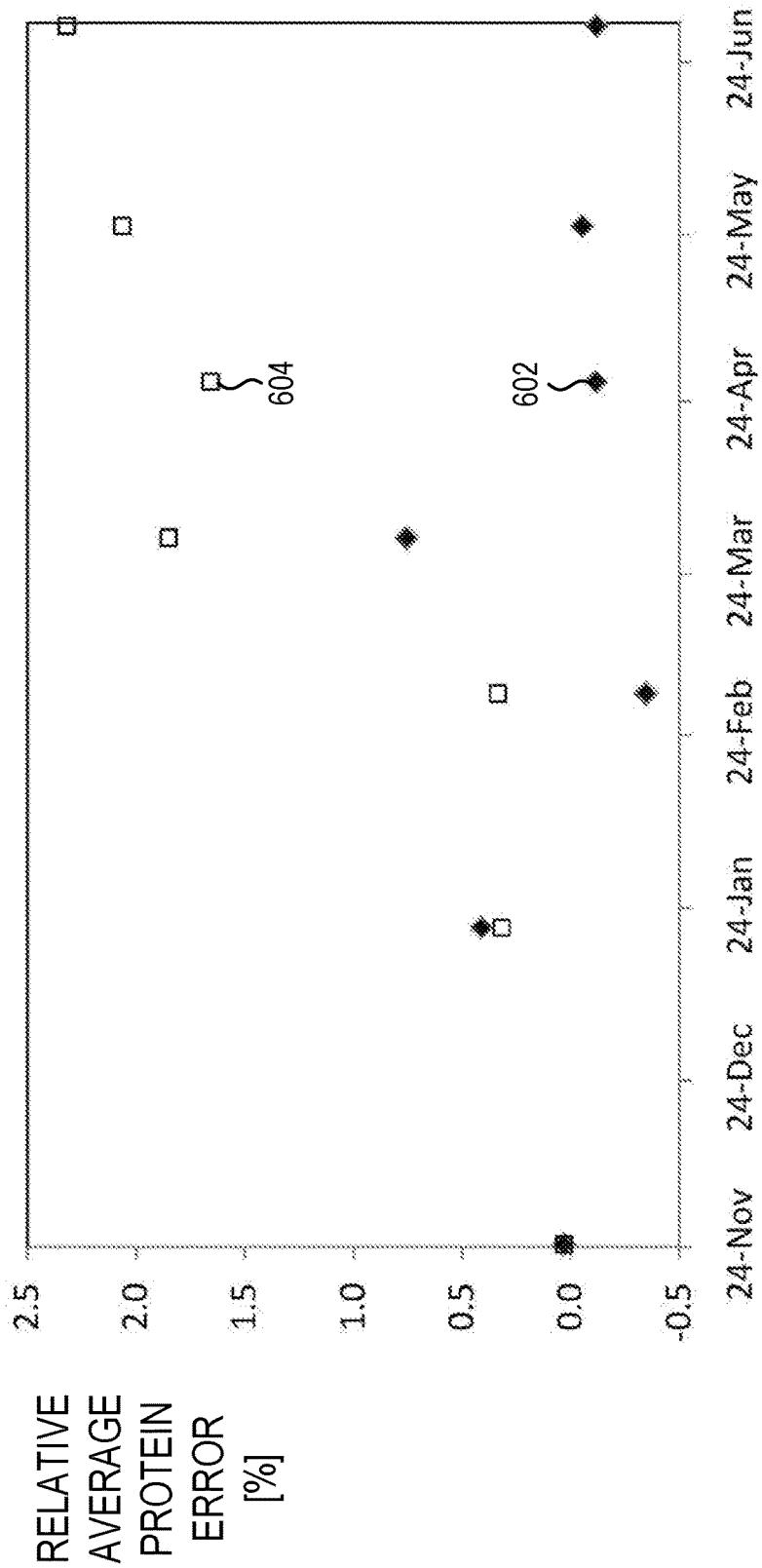
FIG. 6 shows a relative protein error, in percent, for measurements in which the cell width was periodically measured, and corresponding measurements in which the cell width was not periodically measured or updated.
Figure 7:
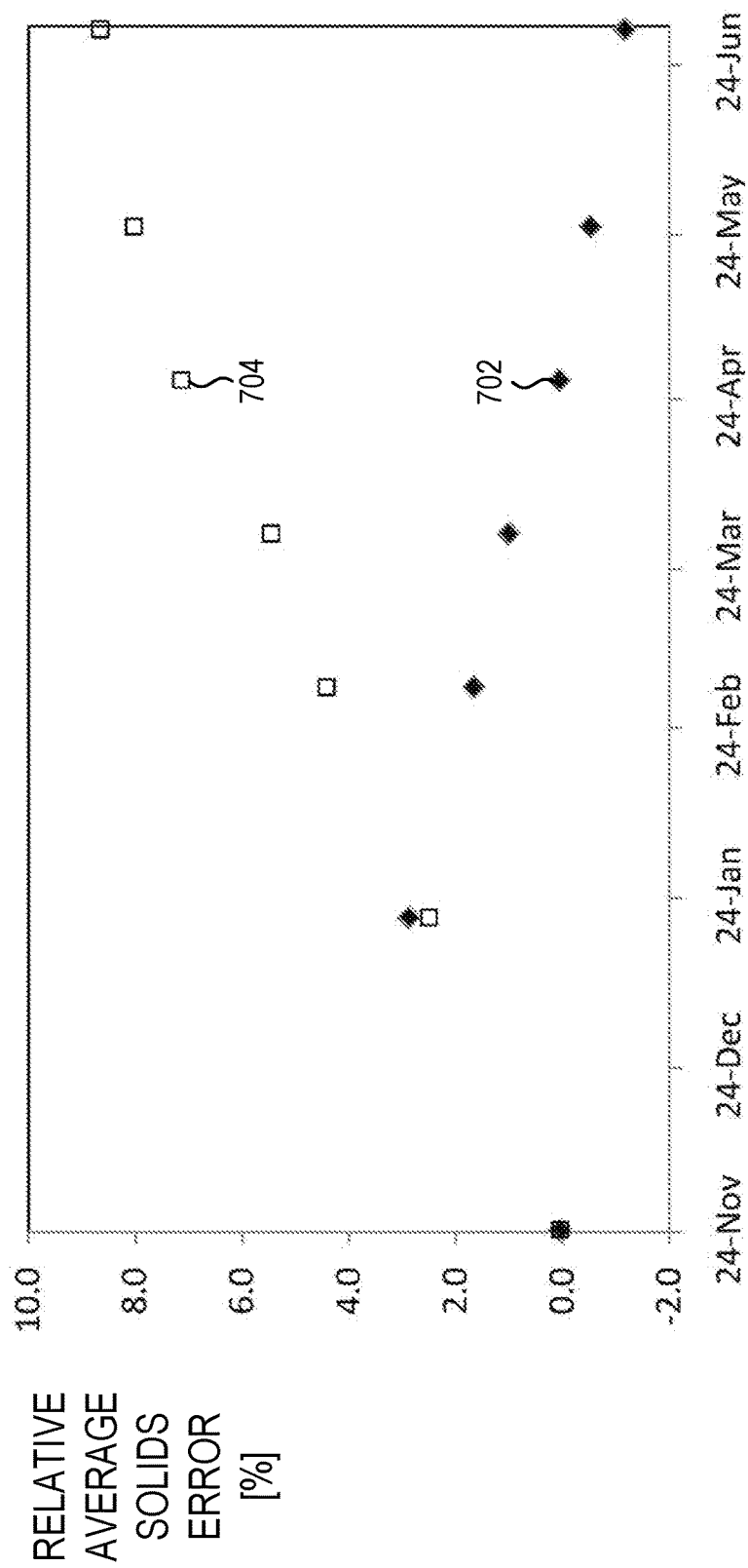
FIG. 7 shows a relative solids error, in percent, for measurements in which the cell width was periodically measured, and corresponding measurements in which the cell width was not periodically measured or updated.

It is beneficial to consider a set of experimental data that shows the effectiveness of periodically measuring the size of the cell, as with the method 200. Data was taken for a milk inspection system over the course of seven months. In this example, the milk inspection system inspected raw milk samples using the mid-infrared portion of the spectrum (e.g., with wavelengths between 3 μm and 10 μm). The system used chemometric calibration methods to relate the measured milk spectrum to a component concentration, for components, such as fat, protein, and solids. The system operated in a relatively demanding environment, running more than 4000 samples per day, with relatively high accuracy, and relatively high potential for cell wear from the high sample volume. The system measured the samples with an accuracy relative standard deviation of less than 1% and a repeatability relative standard deviation of less than 0.25%. In this example, the inspection system tested a set of thirteen reference milk standards over a course of seven months. FIG. 5 shows a relative fat error, in percent, for measurements in which the cell width was periodically measured (502), and corresponding measurements in which the cell width was not periodically measured or updated (504). FIG. 6 shows a relative protein error, in percent, for measurements in which the cell width was periodically measured (602), and corresponding measurements in which the cell width was not periodically measured or updated (604). FIG. 7 shows a relative solids error, in percent, for measurements in which the cell width was periodically measured (702), and corresponding measurements in which the cell width was not periodically measured or updated (704). In each of FIGS. 5-7, the relative error grew with time when the cell width was not periodically measured or updated, but remained relatively small and relatively constant over time when the cell width was periodically measured and updated.

The method 200 for determining the size of the cell 102 of the transmission spectroscopy device 100 has significant advantages over other approaches for determining the size.

For example, a first approach of determining a cell size takes a measurement of a sample of a precisely known composition, measures its absorption at particular wavelengths, and determines the optical path length traversed in the sample from the Beer-Lambert law and from a tabulated molar absorptivity of the compound. This first approach is subject to errors caused by producing, maintaining and delivering samples of precisely known composition. The method 200 discussed herein is not subject to producing, maintaining and delivering samples of precisely known composition, as is required in the first approach.

As another example, a second approach of determining a cell size removes the cell from the device, measures the cell size externally using an interferometer or other suitable measurement device, then returns the cell to the device for future use. This second approach is time-consuming and disruptive, especially for devices that operate in a tightly controlled environment with regulated temperature, pressure, and humidity. The time lost for cell size measurements can be especially problematic for high-volume applications. The method 200 discussed herein can be performed in situ, with a relatively short times required for the measurement.

While the embodiments above have been described as having example designs, inventive aspects of these embodiments can be further modified within the spirit and scope of this disclosure. This application is therefore intended to cover any variations, uses, or adaptations of the embodiments using their general principles. Further, this application is intended to cover such departures from the present disclosure as come within known or customary practice in the art to which this subject matter pertains and which fall within the limits of the appended claims.

What is claimed is:

1. A method for determining a size of a cell of a transmission spectroscopy device, the method comprising:
performing a transmission spectroscopy measurement of a known substance in a cell to produce a measured absorbance spectrum of the known substance, the measured absorbance spectrum of the known substance formed from a ratio of a first emittance scan of the cell to a second emittance scan of the cell, wherein the first emittance scan is taken when the cell is filled with the known substance, and wherein the second emittance scan is taken when the cell is empty, wherein performing the transmission spectroscopy measurement includes draining the known substance from the cell, wherein draining the known substance from the cell comprises, repeatedly:

pumping air through the cell;

illuminating the cell through a first transparent wall of the cell;

measuring a first light through a second transparent wall of the cell; and comparing the first light to a previous measurement of the first light, until a difference between successive measurements of the first light is below a threshold;

subtracting a known absorbance spectrum of the known substance from the measured absorbance spectrum of the known substance to form a fringe pattern, the fringe pattern being oscillatory in amplitude with respect to inverse wavelength, wherein subtracting the known absorbance spectrum includes scaling an amplitude of one of the known absorbance spectrum or the measured absorbance spectrum to match an amplitude of the other of the known absorbance spectrum or the measured absorbance spectrum; and determining a size of the cell from a period of the fringe pattern.

2. The method of claim 1, wherein determining the size of the cell from the period of the fringe pattern comprises calculating the size of the cell to equal 1/(2×p), where quantity p is the period of the fringe pattern.

3. The method of claim 2, wherein determining the size of the cell from the period of the fringe pattern further comprises:

determining inverse wavelength values at which the fringe pattern peaks; and calculating the period to equal a separation between adjacent determined inverse wavelength values.

4. The method of claim 3, wherein calculating the period comprises:

fitting the determined inverse wavelength values to a linear fit;

determining a slope of the linear fit; and setting the period equal to the determined slope.

5. The method of claim 1, wherein performing the transmission spectroscopy measurement of the known substance in the cell comprises:

filling the cell with the known substance;

illuminating the known substance through the first transparent wall of the cell;

measuring a second light from the known substance through the second transparent wall of the cell, opposite the first transparent wall;

producing, from the second light, the first emittance scan;

draining the known substance from the cell;

filling the cell with air;

illuminating the air-filled cell through the first transparent wall of the cell;

measuring a third light from the air-filled cell through the second transparent wall of the cell; and producing, from the third light, the second emittance scan.

6. The method of claim 5, wherein the size of the cell corresponds to a separation between the first and second transparent walls of the cell.

7. The method of claim 5, wherein:

illuminating the known substance comprises illuminating the known substance with light having a broad spectrum; and illuminating the air-filled cell comprises illuminating the air-filled cell with light having the broad spectrum.

8. The method of claim 7, wherein:

the known substance is water; and the broad spectrum includes at least one peak or valley in the known absorbance spectrum of water.

\* \* \* \* \*